US006403778B1

(12) United States Patent
Cunningham et al.

(10) Patent No.: US 6,403,778 B1
(45) Date of Patent: Jun. 11, 2002

(54) TOXICOLOGICAL RESPONSE MARKERS

(75) Inventors: Mary Jane Cunningham, Sunnyvale; Gary B. Zweiger, San Mateo; Scott R. Panzer, Sunnyvale; Jeffrey J. Seilhamer, Los Altos Hills, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/141,825

(22) Filed: Aug. 28, 1998

Related U.S. Application Data

(60) Provisional application No. 60/084,029, filed on May 4, 1998, now abandoned.

(51) Int. Cl.$^7$ ............... C07H 19/00; C07H 21/00; C07H 21/02; C12Q 1/68
(52) U.S. Cl. ............. 536/22.1; 536/23.1; 536/24.3; 536/24.33; 514/1; 514/44; 435/6; 435/68.1
(58) Field of Search ............. 536/22.1, 23.1, 536/24.3, 24.33; 614/1, 44; 435/6, 68.1

(56) References Cited

FOREIGN PATENT DOCUMENTS

| WO | WO 95/206681 | 8/1995 |
|----|----|----|
| WO | WO 97/13877 | 4/1997 |

OTHER PUBLICATIONS

Schena, M. et al., Parallel human genome analysis: Microarray–based expression monitoring of 1000 genes, *Proc. Natl. Acad. Sci.* 93:10614–10619 (1996).

Degawa, M. et al., Metabolic Activation and Carcinogen–DNA Adduct Detection in Human Lyrynx, *Cancer Res.* 54:4915–4919 (1994).

Qu, Shu–Xin et al., Formation and persistence of DNA adducts in different target tissues of rats after multiple administration of benzo[a]pyrene, *Carcinogenesis* 17(1):53–59 (1996).

Chen, J. X. et al., Carcinogens Preferentially Bind at Methylated CpG in the P53 Mutational Hot Spots, *Cancer Res.* 58:2070–2075 (1998).

Greenblatt, M.S. et al., Mutations in the p53 Tumor Suppressor Gene: Clues to Cancer Etiology and Molecular Pathogenesis, *Cancer Res.*, 54:4855–4878, (1994).

Chen, W. et al., Oxidation of Acetaminophen to Its Toxic Quinone Imine and Nontoxic Catechol Metabolites by Baculovirus–Expressed and Purified Human Cytochromes P450 2E1 and 2A6, *Chem. Res. Toxicol*, 11:295–301 (1998).

Kröger, H. et al., Protection From Acetaminophen–Induced Liver Damage by the Synergistic Action of Low Doses of the Poly(ADP–ribose) Polymerase–Inhibitor Nicotinamide and the Antioxidant N–Acetylcysteine or the Amino Acid Lmethionine, *Gen Pharmac.*, 28(2): 257–263 (1997).

Lock, Edward A. et al., Biochemical Mechanisms of Induction of Hepatic Peroxisome Proliferation, *Annu. Rev. Pharmacol. Toxicol.*, 29:145–163 (1989).

Kawashima, H. et al., Protein Expression, Characterization, and Regulation of CYP4F4 and CYP4F5 Cloned from Rat Brain, *Arch. Biochem. Biophys.* 347(1):148–154 (1997).

Database EMBL (Online) embl heidelberg AC#H33194, Sep. 30, 1995, Lee, H.N. et al., "EST108960 rat PC–12 cells", XP002130308.

Lee, N.H. et al., "Comparative expressed–sequence–tag analysis of differential gene expression profiles in PC–12 cells before and after nerve growth factor treatment", *Proc. Natl. Acad. Sci. USA* 92: 8303–8307 (Aug. 1995), XP0020447703.

*Primary Examiner*—Jezia Riley
(74) *Attorney, Agent, or Firm*—Incyte Genomics, Inc.

(57) ABSTRACT

The present invention relates to a composition comprising a plurality of polynucleotide targets. The composition can be used as hybridizable array elements in a microarray. The present invention also relates to methods for screening compounds and therapeutic treatments for toxicological responses.

2 Claims, No Drawings

SEQUENCE LISTING

<160> NUMBER OF SEQ ID NOS: 47

<210> SEQ ID NO 1
<211> LENGTH: 259
<212> TYPE: DNA
<213> ORGANISM: Rattus norvegicus
<220> FEATURE:
<221> NAME/KEY: misc_feature
<223> OTHER INFORMATION: Incyte ID No: 70041686 2F7

<400> SEQUENCE: 1
gtggcggcga tttctgcgtc gagcatttgg agtttcttcg ctgctgaacg g gtagactaa     60 acggcggctg acatggtgga ggaggtacag aagcattctg tgcacacact a gtgttcagg    120 tcattgaaga ggacccatga catgtttgtg gctgataatg gaaaacctgt g cctttggat    180 gaagagagtc acaagcggaa aatggcaatc aagcttcgta atgagtatgg c cctgtgctg    240 catatgccta cttcaaaag                                                  259

<210> SEQ ID NO 2
<211> LENGTH: 295

```
<212> TYPE: DNA
<213> ORGANISM: Rattus norvegicus
<220> FEATURE:
<221> NAME/KEY: misc_feature
<223> OTHER INFORMATION: Incyte ID No: 70050295 7F6
<221> NAME/KEY: unsure
<222> LOCATION: 212, 227, 229, 232, 240, 243 , 245, 250, 257, 267, 269,
      273, 277, 281, 288, 290
<223> OTHER INFORMATION: a, t, c, g, or o ther

<400> SEQUENCE: 2
gcctcttcca ccatccggcc tagtcactgc aggggccatg cctacctatt c cactcaact       60 tgttacctct gcggctccag gcagggctta gtccaacctg cccagacacg g ttcacctt       120 ttatgcccaa gctttcgggg tgctgaggta ggggctgcct tcctgcaccc c caaggagca     180 gacactcaag aatggagtca gctaggaacc cnggagctg cctcatnang c ncttgatan      240 cangnacacn tttgcanctg cagaccntnt tcngaanaac nttgccangn t caac          295

<210> SEQ ID NO 3
<211> LENGTH: 273
<212> TYPE: DNA
<213> ORGANISM: Rattus norvegicus
<220> FEATURE:
<221> NAME/KEY: misc_feature
<223> OTHER INFORMATION: Incyte ID No: 70050450 2F6
<221> NAME/KEY: unsure
<222> LOCATION: 56, 220, 235, 237, 239, 249,  256
<223> OTHER INFORMATION: a, t, c, g, or o ther

<400> SEQUENCE: 3
tgaccctgct tgctgcaggt gactggtcaa gtgcgagcta gcttagttag t gtggngtat      60 aaggcgccat cattcctcca gtaagcctcc atcccaaagc aactgaggct g tggcagtga    120 tgccagcaac ctgtgtcacc caaaattatc cagccctcca cgggcactgc c taggacctg    180 gggagggaag ggactttgca tcacatagcc tcaggttcgn gtttggctct g gtangngnt   240 gcctgaaant ggtggnttcc agctggtgta cgg                                   273

<210> SEQ ID NO 4
<211> LENGTH: 264
<212> TYPE: DNA
<213> ORGANISM: Rattus norvegicus
<220> FEATURE:
<221> NAME/KEY: misc_feature
<223> OTHER INFORMATION: Incyte ID No: 70050517 0F6

<400> SEQUENCE: 4
ggctggtctg cgatggcccg ctacctcggc tcgctggaac catgtgtggg t ccggcactt      60 gagactggaa tcctgaaagg ggtgaacctt cagcggaaac ttgcggcaaa t tttactccg    120 tccggacagc cacggcggga ggaggcagtg aatgctttgt gctggggcac a ggcggcgag    180 acccagattt tggtgggatg tgcggacagg accgtgaggc actttaatgc g gaggagggt  240 acattccaga ccagagatac tgcc                                              264

<210> SEQ ID NO 5
<211> LENGTH: 268
<212> TYPE: DNA
<213> ORGANISM: Rattus norvegicus
<220> FEATURE:
<221> NAME/KEY: misc_feature
<223> OTHER INFORMATION: Incyte ID No: 70051117 0F6
<221> NAME/KEY: unsure
<222> LOCATION: 231
<223> OTHER INFORMATION: a, t, c, g, or o ther
```

```
<400> SEQUENCE: 5
ggcaacaaga cgctgtgatt ggaagcaatg acgaagtcct cacactccgg g gagtgggta        60 tgtgctgcta catcatgtga tgggcagcct ggaggggatg cagggcgcct g gagctatgt       120 ccagggtggc atgggtgccc tctcagatgc cattgcaagc tcggctactg c acatggagc      180 aagtatcttc acagagaaga ctgtggctaa ggtgcaagtg aacagcgaag n cgtgtccaa      240 ggggtcgtgc tcagggccgg cgaggagt                                           268

<210> SEQ ID NO 6
<211> LENGTH: 284
<212> TYPE: DNA
<213> ORGANISM: Rattus norvegicus
<220> FEATURE:
<221> NAME/KEY: misc_feature
<223> OTHER INFORMATION: Incyte ID No: 70060782 7F7
<221> NAME/KEY: unsure
<222> LOCATION: 28, 37, 44, 67, 71, 88, 1 02, 172, 238
<223> OTHER INFORMATION: a, t, c, g, or o ther

<400> SEQUENCE: 6
gtgtacctac ctgctgagga aggaaggngt ggatggnacc cagnaacctg a tgtccagca        60 caagggnaac nggcgtggct ttctaatnta caagcctggg tnactacagc t tgcagctac      120 ctaacccatg caggaggcga accctctgag cccagttgct attgtgacca t naagatgtc      180 ttgccacaca gcttccaccc agtctgggtt taatgggaag ttacctaacg a ttacccnca      240 gaagacacat gagacgcttg cttcaaagct ctcggatgca gcca                         284

<210> SEQ ID NO 7
<211> LENGTH: 243
<212> TYPE: DNA
<213> ORGANISM: Rattus norvegicus
<220> FEATURE:
<221> NAME/KEY: misc_feature
<223> OTHER INFORMATION: Incyte ID No: 70050081 4F6

<400> SEQUENCE: 7 acttttcta atgtcttatg gccacttctt atgagaatgg ggagctgctc t gcctgaggg         60 tcgtgagagg aagcgccaga gcaggcccat catcccaacc cttggccttg g cccttcccc      120 ctagctctgc agcatttctt cagatcctct ttcctgagag tcaaggagac t aaacaccaa      180 taaaccagac acaaccttcg tggccccaaa ggagaaaccg attagagggt t ctctgctag      240 atg                                                                      243

<210> SEQ ID NO 8
<211> LENGTH: 259
<212> TYPE: DNA
<213> ORGANISM: Rattus norvegicus
<220> FEATURE:
<221> NAME/KEY: misc_feature
<223> OTHER INFORMATION: Incyte ID No: 70052681 9F6
<221> NAME/KEY: unsure
<222> LOCATION: 235
<223> OTHER INFORMATION: a, t, c, g, or o ther

<400> SEQUENCE: 8
ggcgcaggcg aaggggcct gtcaccgtcc gctgcgacgt cgcggctgga g ttgaacctg         60 gtgccggctg ctttgcgctg tgagtcgatg gcggccgaaa acgagaacc g gacgagtgg       120 cgtctggaga agtatgtggg tccctggaag acatgctgca gccctgaaag t ccaagcaag      180 taaaccgcct cggaagtgat cagtgagtac tcccgcaaag tgactttctg a aggnatgct      240
```
gaggctgaga agtgactct                                              259

<210> SEQ ID NO 9
<211> LENGTH: 255
<212> TYPE: DNA
<213> ORGANISM: Rattus norvegicus
<220> FEATURE:
<221> NAME/KEY: misc_feature
<223> OTHER INFORMATION: Incyte ID No: 70052817 6F6
<221> NAME/KEY: unsure
<222> LOCATION: 2, 4, 53, 55, 86, 88, 92,  106, 133, 211, 214
<223> OTHER INFORMATION: a, t, c, g, or o ther

<400> SEQUENCE: 9
cnanggccct cagggaatca agaggagcca gcctgatccc tggcctctgg a gncntaaaa        60 caagtgtgtt tttgcaggta gcctangntg gntgtcgatg gagctncagc c tgcatggca       120 ttaggcagga agncactctg gatgattgtg cacatgagaa cctagtcagg g agggaggt        180 ttaaggagag gcttagaata caagtgagaa ncancgagaa agggaccaag t cctcagaat       240 agaagctatc tgcct                                                         255

<210> SEQ ID NO 10
<211> LENGTH: 269
<212> TYPE: DNA
<213> ORGANISM: Rattus norvegicus
<220> FEATURE:
<221> NAME/KEY: misc_feature
<223> OTHER INFORMATION: Incyte ID No: 70052808 2F6
<221> NAME/KEY: unsure
<222> LOCATION: 30-31, 140
<223> OTHER INFORMATION: a, t, c, g, or o ther

<400> SEQUENCE: 10
ataaaagtga aaactgggca agggcaaggn ngctgggcgt gaaccgctta c tagataatg        60 gtctctaaaa attggctctg aaaaccctgt ttgtgtattc gttttatgag t gcttaaaaa       120 tggtgtgacc agggcatggn cactgtcatt ggaacagcaa catgcttgct g gcacattgg       180 aatggggaaa tgtgaagaaa gctggcatca ggcctgcggc acccatttct t tgatgaaag      240 tgttgtgtca aaccccccact aatcatttt                                         269

<210> SEQ ID NO 11
<211> LENGTH: 254
<212> TYPE: DNA
<213> ORGANISM: Rattus norvegicus
<220> FEATURE:
<221> NAME/KEY: misc_feature
<223> OTHER INFORMATION: Incyte ID No: 70053532 8F6
<221> NAME/KEY: unsure
<222> LOCATION: 36, 47, 67, 80, 82-83, 92, 111
<223> OTHER INFORMATION: a, t, c, g, or o ther

<400> SEQUENCE: 11
caaggcgttc tgctgcgaga acgacattga catcgngcgc gtggtanacg t gcggaggct        60 ggcggcnatc gtgggcgccn annacgagag gngcgcgccg tgagacttgc n ttgcatcct      120 catttcgaac cctaatgaag acacatggaa ggaccctgcc ttggagaagc t cagtttgtt      180 ctgcgaggag agccgcagct tcaacgactg ggtcccagca tcacccttcc g agtgacagc      240 ctgcagggac cttg                                                          254

<210> SEQ ID NO 12
<211> LENGTH: 244
<212> TYPE: DNA
<213> ORGANISM: Rattus norvegicus

```
<220> FEATURE:
<221> NAME/KEY: misc_feature
<223> OTHER INFORMATION: Incyte ID No: 70036897 3F6
<221> NAME/KEY: unsure
<222> LOCATION: 50, 102, 169, 171, 204, 210,  234, 242
<223> OTHER INFORMATION: a, t, c, g, or o ther

<400> SEQUENCE: 12
cacaatccca aactggaaaa acttaaaaag gaatcctgct gtgaaaggtn t atattactc      60 tagatttttc ttactgtaaa tattgtaaga ttgtaatact gncaatattt t attaaccaa    120 caaatgttaa tctatgtgaa atcagactta tttaaagggc tgctattang n gtgtggccc    180 tttgctgaca gattaagtat attntgagtn agataactta ttaaggatgg a acnttaaag   240 gntc                                                                 244

<210> SEQ ID NO 13
<211> LENGTH: 237
<212> TYPE: DNA
<213> ORGANISM: Rattus norvegicus
<220> FEATURE:
<221> NAME/KEY: misc_feature
<223> OTHER INFORMATION: Incyte ID No: 70036897 4F6
<221> NAME/KEY: unsure
<222> LOCATION: 11, 20, 132, 136, 149, 151, 158, 171, 173, 184, 187,
      190, 193, 196, 204-205, 208, 212 -213, 215, 221, 227, 230-231, 236
<223> OTHER INFORMATION: a, t, c, g, or o ther

<400> SEQUENCE: 13
gtccttagct ngtgggcggn ggggtgcagt ctgctactat ctgaacgaat t taatgtggg     60 agcatgcctt atacaacaca ggaaattaat gtgtgatcta atgcgtgatc t atgacttat   120 tacaatacag anttangtgt gaacctgcnt ncaaaacngg tcagaattt t n gnaatggcc  180 ggantgnacn ggntgnttat taanntgnaa gnngntggga naggccnggn n tgcgnt      237

<210> SEQ ID NO 14
<211> LENGTH: 235
<212> TYPE: DNA
<213> ORGANISM: Rattus norvegicus
<220> FEATURE:
<221> NAME/KEY: misc_feature
<223> OTHER INFORMATION: Incyte ID No: 70036946 1F6
<221> NAME/KEY: unsure
<222> LOCATION: 38, 49, 53, 55, 107, 125, 132, 136, 138, 150-151, 163,
      165-166, 170, 179-180, 184, 186, 189, 192, 199, 219-221, 223
<223> OTHER INFORMATION: a, t, c, g, or o ther

<400> SEQUENCE: 14
ctttaaccgg tgggctgctg taagaatcgg tggcaggnct ctctctgcng g gngntaatt    60 gctctggaac gctactagga cccgaatact aaggccacat ctctacngtc t aagagggga  120 aatangatag cnttgntncc acatgtggcn nagtggggtt gcngnntatn g cttaacann  180 tacnanttnc antgattant gtggtggtaa gatggcttnn ntnaaaactg c cgcc       235

<210> SEQ ID NO 15
<211> LENGTH: 205
<212> TYPE: DNA
<213> ORGANISM: Rattus norvegicus
<220> FEATURE:
<221> NAME/KEY: misc_feature
<223> OTHER INFORMATION: Incyte ID No: 70078257 9F6
<221> NAME/KEY: unsure
<222> LOCATION: 17, 19, 21, 56, 69, 75, 8 1, 103, 109, 111, 122, 127,
      130, 137, 144, 148, 151, 153, 166, 174, 177, 190, 193, 195
<223> OTHER INFORMATION: a, t, c, g, or o ther

<400> SEQUENCE: 15
```

```
gggtcattta caacctntna nacaagggga cgcccccaga catgccagtg t tcacngaac        60 aagatgcang tccancagga ncagatagac tcagtccatg gantggctna n caaccagcc       120 cngggcngcn caactgntgg acangtangg nantttctgc gacaantggt g agnttnttg       180 cgaagctccn tgncngaaag aatgg                                              205
```

<210> SEQ ID NO 16
<211> LENGTH: 236
<212> TYPE: DNA
<213> ORGANISM: Rattus norvegicus
<220> FEATURE:
<221> NAME/KEY: misc_feature
<223> OTHER INFORMATION: Incyte ID No: 70078266 5F6
<221> NAME/KEY: unsure
<222> LOCATION: 11-12, 33-34, 46, 76, 85-86, 103, 123, 127, 144, 152,
      157, 162, 167, 169, 174, 183-184 , 186, 191-194, 217, 224, 230
<223> OTHER INFORMATION: a, t, c, g, or o ther

<400> SEQUENCE: 16

```
ggtctccatg nngaccgggc gccttggggt tgnngagacg ctgcangccc t taacgcccg       60 cttgtagggc ccttgnaacc ccggnntggt ttaaggaaaa cgnatgcccg a caccttcgt      120 gtncganact ttttggcacc gcgnaaactc gnttacngtg gnttttnang t agngggtat     180 gtnncncgag nnnntttagg ccggcttgtg ctgcggnatt gggntgaaan t gtctg         236
```

<210> SEQ ID NO 17
<211> LENGTH: 267
<212> TYPE: DNA
<213> ORGANISM: Rattus norvegicus
<220> FEATURE:
<221> NAME/KEY: misc_feature
<223> OTHER INFORMATION: Incyte ID No: 70048092 7F6

<400> SEQUENCE: 17

```
ctggaccaac atcacaagaa atgaataaag cagatttctc tgttgagttc t gcagtaaac      60 cacctaaaag ccaatgtcaa gtcagccgca gacttactta gcctgcctag c actgtagag    120 ggacttcaga agagtgtcgc ttccattggc aatacgttga acagtgtcag c cttgctgta   180 gaggcaatac agaagaccgt ggatgaacac aaggcacctt ggagttactg c agggcagtg   240 tggagaccaa tggaagcaac caaatca                                            267
```

<210> SEQ ID NO 18
<211> LENGTH: 271
<212> TYPE: DNA
<213> ORGANISM: Rattus norvegicus
<220> FEATURE:
<221> NAME/KEY: misc_feature
<223> OTHER INFORMATION: Incyte ID No: 70048173 2F6
<221> NAME/KEY: unsure
<222> LOCATION: 2, 92, 162, 181, 247-248, 25 3, 256, 262, 269
<223> OTHER INFORMATION: a, t, c, g, or o ther

<400> SEQUENCE: 18

```
gncttattta tgtatgaaaa tgcagaaatc tgtacattcc tcaagccagt c ctgtcgagc      60 caggtctgtc ccatccttgt acctcaaccc antcccacct ggcctgaaca c cccatgaga   120 cagagctggt ctctgggctg ggccccccag gcctgggctg gncaggcaga c cctaccccg   180 nagtccactg gctccagtct ccgaggctct cctgggctac aaaggggggac acacacacc     240 cagaatnntt tantgnattg gngggcccng g                                       271
```

<210> SEQ ID NO 19

<211> LENGTH: 283
<212> TYPE: DNA
<213> ORGANISM: Rattus norvegicus
<220> FEATURE:
<221> NAME/KEY: misc_feature
<223> OTHER INFORMATION: Incyte ID No: 70048314 3F6
<221> NAME/KEY: unsure
<222> LOCATION: 37, 131, 199, 205-206, 208, 232-233, 239, 244-246, 251,
      253-254, 258, 261-262, 266, 269, 274-275, 280
<223> OTHER INFORMATION: a, t, c, g, or o ther

<400> SEQUENCE: 19
ctaaaattaa gatagaagtg aatgagacag atatctngta agacactgta t tttcttgtg        60 tgatcagatc tagtgtggtg ggatgataga agttgaactt gctttattgc t atgggttaa      120 aatattttgt ntcattaaaa tggcctattg aaatgctttt ctgttcctat a ataaaataa      180 cctgatgaaa aagtaaaana aaaannanaa aaaaaaaggg gcggccccg c nnagggcnt       240 tttnnnccg ngnnttantt nngccnggnc cctnngggn cca                           283

<210> SEQ ID NO 20
<211> LENGTH: 256
<212> TYPE: DNA
<213> ORGANISM: Rattus norvegicus
<220> FEATURE:
<221> NAME/KEY: misc_feature
<223> OTHER INFORMATION: Incyte ID No: 70048453 8F6

<400> SEQUENCE: 20
ctggcctcag cttcctaagt tctgggagtc ggacaggtgt ttgccacaca c atggcccac       60 cggggaccta gaacctacag tgaaccgtca cccaggctct gtggatgttc t gcatcctga     120 ggtagacagc ctctaatatc ctgttaggga cctaggacca gagctggggt g cccaggcat     180 gtcccaacat gtcgcatcgg ccacagggat atcggttgaa gtgcatttgg a agtgtgctg     240 ggacgccagc cagctt                                                       256

<210> SEQ ID NO 21
<211> LENGTH: 272
<212> TYPE: DNA
<213> ORGANISM: Rattus norvegicus
<220> FEATURE:
<221> NAME/KEY: misc_feature
<223> OTHER INFORMATION: Incyte ID No: 70048007 7F6
<221> NAME/KEY: unsure
<222> LOCATION: 64, 68, 124, 140, 145, 213, 260, 267, 269
<223> OTHER INFORMATION: a, t, c, g, or o ther

<400> SEQUENCE: 21
ctgacctgac ccatgattta aggaccgtag tttagcacgg accactgcaa a ggcgggcta      60 aggnctgntg ggctaaaggt ctctttgagc ccagtggcta tagtcacacc t tctttgctc    120 tggnccagga ggcctacttn ttctntactc gtggaatcct ggaatcttaa a gataaaaga    180 acctagaaag aaaatcaaac ccactttcct tgngggcaga tggtaatatg g gactgagac    240 agcaaacctg gggcttggan aggaccnanc tc                                    272

<210> SEQ ID NO 22
<211> LENGTH: 270
<212> TYPE: DNA
<213> ORGANISM: Rattus norvegicus
<220> FEATURE:
<221> NAME/KEY: misc_feature
<223> OTHER INFORMATION: Incyte ID No: 70006020 7F7
<221> NAME/KEY: unsure
<222> LOCATION: 40, 44, 46, 114
<223> OTHER INFORMATION: a, t, c, g, or o ther

<400> SEQUENCE: 22

```
taccctgca tgggataccg tttctcgacc ccagtgcacn tggntnctgt c atcccatga      60 aattgcagca agggcagtct cttttgtggg aacagattaa ctcctacaca t gangtagat    120 tcaacacctg ccaggaaagc agaagcatta cttaagtgtc ctgtgaaggc a aacatcaag   180 tcaattcagc ttatcttgaa gagtggcaaa ccatgaactc caaatgtcat t gtgtgaaac   240 tgaacgatgg tcatttcatt ccggtgctgg                                     270
```

<210> SEQ ID NO 23
<211> LENGTH: 250
<212> TYPE: DNA
<213> ORGANISM: Rattus norvegicus
<220> FEATURE:
<221> NAME/KEY: misc_feature
<223> OTHER INFORMATION: Incyte ID No: 70013310 5F6
<221> NAME/KEY: unsure
<222> LOCATION: 45, 49-50
<223> OTHER INFORMATION: a, t, c, g, or o ther

<400> SEQUENCE: 23

```
ccctcctgta tctgaaccca gcttctcagc tctgagatga gtgcnggann g gcttcccaa    60 cctatgctca ataccacagg cagcctgcag gagggagaaa tgggtaaaat g ttccatggg   120 aaatgtctca gaatcgtctc ccccgaatct cctgctaagc tttactgctg c tatggagtg   180 atcatggtcc tcagtgtagc tgtagttgct cttctgttg ctttgtcagt a aaaatgaca   240 ccacagatct                                                           250
```

<210> SEQ ID NO 24
<211> LENGTH: 226
<212> TYPE: DNA
<213> ORGANISM: Rattus norvegicus
<220> FEATURE:
<221> NAME/KEY: misc_feature
<223> OTHER INFORMATION: Incyte ID No: 70013811 7F6

<400> SEQUENCE: 24

```
gaggattcac tcacatttgc ttcccgctgg ccatgagtga gctgcccttt c tgagtccag    60 agggagccag agggcctcac aacaacagag ggtctcagag ctccctggag g aaggctcag   120 ttacaggctc agaggctcgg cacagcttag gtgtcctgaa tgtgtccttc a gcgtcagca   180 accgtgtcgg gccctggtgg aacatcaaat catgccagca gaagtg               226
```

<210> SEQ ID NO 25
<211> LENGTH: 265
<212> TYPE: DNA
<213> ORGANISM: Rattus norvegicus
<220> FEATURE:
<221> NAME/KEY: misc_feature
<223> OTHER INFORMATION: Incyte ID No: 70026878 8F6
<221> NAME/KEY: unsure
<222> LOCATION: 85
<223> OTHER INFORMATION: a, t, c, g, or o ther

<400> SEQUENCE: 25

```
cggaggtgct cccaggcggc tgcactggct cggaggagta gcaggaggag c tccgcgcag    60 gaacaaacct ggaggcaaac caganggagg caatgtttga atgactgtaa g aagaccaga   120 cagtgaaaat gtcagccctc aactggaagc cctttgtgta cggagggctg c ctccatcac   180 cgcagaatgt ggtacatttc caattgattt gactaagact cggcttcaga t tcaaggcca   240 gacaaatgat gccaagttcc gagag                                          265
```

<210> SEQ ID NO 26
<211> LENGTH: 257
<212> TYPE: DNA
<213> ORGANISM: Rattus norvegicus
<220> FEATURE:
<221> NAME/KEY: misc_feature
<223> OTHER INFORMATION: Incyte ID No: 70027092 4F6
<221> NAME/KEY: unsure
<222> LOCATION: 58, 99
<223> OTHER INFORMATION: a, t, c, g, or o ther

<400> SEQUENCE: 26
ctgggatccc cagggctaat gggcatcctg ttcttgcagc agggcactgt g agaaagnct      60 ctcaccgtga ccaagtttct ctgagtgtcc agccaaccna ggctcaccag c tccctccag     120 ctaccgcccg tccatcaggt cagctgccaa ccccaggctg aacaccaacc c cagctatga    180 gctcctggag gcatgactcc ctcagggcca gcagctccga tcccctccca g tagttatca    240 ttggcaatgg ccctcgg                                                     257

<210> SEQ ID NO 27
<211> LENGTH: 244
<212> TYPE: DNA
<213> ORGANISM: Rattus norvegicus
<220> FEATURE:
<221> NAME/KEY: misc_feature
<223> OTHER INFORMATION: Incyte ID No: 70030372 2F6
<221> NAME/KEY: unsure
<222> LOCATION: 2, 8, 50, 56, 63, 76, 177 , 219, 233, 240
<223> OTHER INFORMATION: a, t, c, g, or o ther

<400> SEQUENCE: 27
gncgaggnca ccaaggtgtt tctgcctcta cttagaaagt ccaaggggan g ctggntaac     60 gtnagcagca tgggaanccat gattccattt cagatgatgg ccgcctacgc c tgcacgaag   120 gcagctataa gcatgttctc agcccgtcat caggcaagag cttccaaatg g ggagtnaaa   180 gcgggaccat cattctggag cttcaaacca acatcgtang ctcacaggac a gntgggatn   240 aaag                                                                  244

<210> SEQ ID NO 28
<211> LENGTH: 263
<212> TYPE: DNA
<213> ORGANISM: Rattus norvegicus
<220> FEATURE:
<221> NAME/KEY: misc_feature
<223> OTHER INFORMATION: Incyte ID No: 70050204 7F6

<400> SEQUENCE: 28
ggaaatgact ggtctgaagc ggcttggcag cctgagcagt caggtactgc g gctctactg     60 gcactgcctg agggtccaag gactgtggtg attctcatgg aggaccctga g atttctgca   120 atctgatcag tgtcaaatgc cactggattc gctctgagac tcttgcccta g aggatggcc   180 aaagggctcc tgatgaccta tgcccttttgg cttttggggc cctgttggac t acaccacct  240 gtatctggga agggacagcc atc                                             263

<210> SEQ ID NO 29
<211> LENGTH: 259
<212> TYPE: DNA
<213> ORGANISM: Rattus norvegicus
<220> FEATURE:
<221> NAME/KEY: misc_feature
<223> OTHER INFORMATION: Incyte ID No: 70050226 0F6
<221> NAME/KEY: unsure
<222> LOCATION: 52, 137, 167, 189, 235, 254, 256
<223> OTHER INFORMATION: a, t, c, g, or o ther

<400> SEQUENCE: 29

| ggactacccc caccatgccc gtgtcattga gactctgatt gtccactatg g nctggtctt | 60 |
| tgaggaggag ccagaagaag cagctggcag ccaagagggg gcgtccgcca g tgtgcccag | 120 |
| ctggagactg ctgaggncat tgtcttcccc cagcaggagg aggcggncga t ggaaaccga | 180 |
| gaatcccang tgcatcaatg actcagactc agagctggaa gaggcttctg a cctntttcg | 240 |
| cctcggacgc cacncnctc | 259 |

<210> SEQ ID NO 30
<211> LENGTH: 260
<212> TYPE: DNA
<213> ORGANISM: Rattus norvegicus
<220> FEATURE:
<221> NAME/KEY: misc_feature
<223> OTHER INFORMATION: Incyte ID No: 70014221 3F6
<221> NAME/KEY: unsure
<222> LOCATION: 140, 158, 161, 170-171, 177, 191, 193, 199, 203,
    206-207, 212, 217-218, 220, 224, 226, 231, 238, 243, 246, 248,
    253, 255, 258
<223> OTHER INFORMATION: a, t, c, g, or o ther

<400> SEQUENCE: 30

| cacagggttt tccccaagag cacgcctctt tacttcaggg aattctcgga a actttcagg | 60 |
| attcggggg cttccctggg aggagacgag agaggattag aagcggacat c cacggcttc | 120 |
| tgtgatgac cacgcctttn gtctttgcta gaactctntg ngacttcccn n ggtganttc | 180 |
| taatcacgga ntncacgcna agnttnngga antacgnngn cccntnaaga n aaacacntt | 240 |
| ttnggngngg ggnanaanct | 260 |

<210> SEQ ID NO 31
<211> LENGTH: 288
<212> TYPE: DNA
<213> ORGANISM: Rattus norvegicus
<220> FEATURE:
<221> NAME/KEY: misc_feature
<223> OTHER INFORMATION: Incyte ID No: 70022955 5H1

<400> SEQUENCE: 31

| caggagtacc actcacaggc cacctggcag gaagagataa gcccccagcc c ccgacatcc | 60 |
| aggacgcccc gaacctgcca atgtgtgtag ctataccttta ttacctcatc a tgtgaaata | 120 |
| gccaatcata tgtgaacatg tctatgtgcc tcgtttgaat ccaccaatcc c tgtaactat | 180 |
| gcatctgctt ctgtacgcct gcttctgctt ccccaatccc tataaaagcc c catgctgga | 240 |
| gctgctgggc gcgcaagtcc tcctaagaga ctgtgtgccc gcagtacc | 288 |

<210> SEQ ID NO 32
<211> LENGTH: 258
<212> TYPE: DNA
<213> ORGANISM: Rattus norvegicus
<220> FEATURE:
<221> NAME/KEY: misc_feature
<223> OTHER INFORMATION: Incyte ID No: 70062683 9H1
<221> NAME/KEY: unsure
<222> LOCATION: 53, 244
<223> OTHER INFORMATION: a, t, c, g, or o ther

<400> SEQUENCE: 32

| gggtgcgcgt ggagttgcgc atgcgccttc ccgccgcgca gggcaaaggt g gnggcgctc | 60 |
| tggtgaatgg ttggttgctg tgcaagagcg ttttctggct tttggtggcg a aggcggcct | 120 |

```
ggccgcgagg tgcagctgct ggtgggcagg tgtactaatg tctacagact atgagctttc      180
agaatctctg gagagagtac aaagttctgc atgttatggt accttttaatc gggttcatac     240 attngggtgg cacagaat                                                    258
```

<210> SEQ ID NO 33
<211> LENGTH: 268
<212> TYPE: DNA
<213> ORGANISM: Rattus norvegicus
<220> FEATURE:
<221> NAME/KEY: misc_feature
<223> OTHER INFORMATION: Incyte ID No: 70062789 0H1
<221> NAME/KEY: unsure
<222> LOCATION: 7, 11, 40, 53, 150
<223> OTHER INFORMATION: a, t, c, g, or o ther

<400> SEQUENCE: 33

```
gtacaangag ngccggggct tgggtctagt tggaggggan gcagtggcca g tncagggct      60 cagatgagag agttagccga gttaggggca gctactagga tgggggcagg a ggagaagcg    120 gggctaacta taaagaagac tagatttcgn cacagtgggg atgtgaagg c agctttcaa    180 accgccttg tcaaacaaca cagggccagc agccttcaag accaggctat c cctgccgtc    240 tgctggcatg ggggcacttg taccgtcc                                        268
```

<210> SEQ ID NO 34
<211> LENGTH: 299
<212> TYPE: DNA
<213> ORGANISM: Rattus norvegicus
<220> FEATURE:
<221> NAME/KEY: misc_feature
<223> OTHER INFORMATION: Incyte ID No: 70005910 5H1

<400> SEQUENCE: 34

```
tcatcacaac ccaactgtgt ggccaaatcc agaggtgttt gacccttatc g atttgcacc     60 agagtcttcc cgacacagcc actcattcct gcccttctca ggaggagcaa g gaactgcat   120 tgggaaacag tttgccatga atgaactgaa ggtggccgtg gccctgaccc t gctccgctt   180 tgagctgctg ccagatccca ccaggatccc aatccccata ccaagactcg t gttgaagtc   240 caagaatggg atctacctgc gtctcaaaaa gctccaataa tcttgacagc a caagacag    299
```

<210> SEQ ID NO 35
<211> LENGTH: 300
<212> TYPE: DNA
<213> ORGANISM: Rattus norvegicus
<220> FEATURE:
<221> NAME/KEY: misc_feature
<223> OTHER INFORMATION: Incyte ID No: 70005961 0H1

<400> SEQUENCE: 35

```
aaacaacctg actttcttgc gtgtgaggag tgccttttat gggaacagca t catctacaa     60 tatgtcctct gatggccgtt tgtcccgccg ggcctgccag attgctcatg a gcacacaga   120 tggagtgatc aaaatgagga aggctcagct gcagaatgag aagagcttc a gaaggccag    180 gaagaagagg cacttggatt tcctggacat cctgttgttt gccaaaatgg a ggatgggaa   240 gagcttgtct gatgaggacc tgcgtgcaga ggtggacaca ttcatgtttg a gggtcatga   300
```

<210> SEQ ID NO 36
<211> LENGTH: 296
<212> TYPE: DNA
<213> ORGANISM: Rattus norvegicus
<220> FEATURE:

```
<221> NAME/KEY: misc_feature
<223> OTHER INFORMATION: Incyte ID No: 70005963 0H1

<400> SEQUENCE: 36
gggtttctct gtatttaccc ctacaagatc cctggatggt gtctctgggt t cttccaagg      60 ggccttcctg ctcagtctat ttctggtgct gttcaaggca gtccaattct a cttacgaag    120 gcaatggctc tcaaggccc tcgagaagtt cccatccacg ccttcccact g gctttgggg    180 ccacgacctg aaggacagag aattccagca ggttcttacg tgggtagaga a attcccagg    240 tgcctgctta cagtggctct cagggagcaa aacacgagtc ctgctctatg a ccctg         296

<210> SEQ ID NO 37
<211> LENGTH: 286
<212> TYPE: DNA
<213> ORGANISM: Rattus norvegicus
<220> FEATURE:
<221> NAME/KEY: misc_feature
<223> OTHER INFORMATION: Incyte ID No: 70006295 9H1
<221> NAME/KEY: unsure
<222> LOCATION: 204
<223> OTHER INFORMATION: a, t, c, g, or o ther

<400> SEQUENCE: 37
ggcccatgga gcacacccag gctgtggact atgttaagaa gctgatgacc a agggccgct    60 actcactaga tgtgtggagt aggagctacc accctcccac ccctcgctcc c tgtaatcac   120 ctaacttctg ccgacctcca cctctggtgg ttcctgcctg gctggacac a gggaggccc   180 agggactgac tcctggcctg agtngtgccc tcctgggccc ctaagcagag t ccggtccat   240 tgtatcaggc agcccagccc caaggcacat ggcaagaggg attgac                    286

<210> SEQ ID NO 38
<211> LENGTH: 289
<212> TYPE: DNA
<213> ORGANISM: Rattus norvegicus
<220> FEATURE:
<221> NAME/KEY: misc_feature
<223> OTHER INFORMATION: Incyte ID No: 70060645 9H1

<400> SEQUENCE: 38
ggtgagtccc gtgtggagaa aatatacaag taagaccgct acgtgcctgg c gactggaga    60 tgtgatgggg cacagcgcac agagagccat aatggcctca tcgtacaggt c tgggacgct   120 cagcaacacc ccagcaggca ctgcactgtc tagtggacaa gctctgttag c aggaagagc   180 ttctctgcgt ctgtccaaga aaggctggtc aaggctccct accacctaca c atactgtgg   240 ttggagaaat caaggttcct ggcaaaagag agtagcttca cgggaggca                 289

<210> SEQ ID NO 39
<211> LENGTH: 79
<212> TYPE: DNA
<213> ORGANISM: Rattus norvegicus
<220> FEATURE:
<221> NAME/KEY: misc_feature
<223> OTHER INFORMATION: Incyte ID No: 70060888 2H1
<221> NAME/KEY: unsure
<222> LOCATION: 39, 48, 66, 68, 72
<223> OTHER INFORMATION: a, t, c, g, or o ther

<400> SEQUENCE: 39
cttaacgctc ctgccacgcc gcctccgccc gtgcaatgnc tctgtagncg g cgatctacg    60 tacgtntncc cngccccgt                                                   79
```

<210> SEQ ID NO 40
<211> LENGTH: 248
<212> TYPE: DNA
<213> ORGANISM: Rattus norvegicus
<220> FEATURE:
<221> NAME/KEY: misc_feature
<223> OTHER INFORMATION: Incyte ID No: 70048398 8H1
<221> NAME/KEY: unsure
<222> LOCATION: 8, 21, 24, 35, 40, 52, 78 , 90, 104, 137, 169, 209, 220
<223> OTHER INFORMATION: a, t, c, g, or o ther

<400> SEQUENCE: 40

| | | | | | |
|---|---|---|---|---|---|
| tttagttnca | atcatggagg | nctntcaggt | gaggnccnta | ctcccaaagc | c ngcgctgag | 60 |
| tctacaactt | ctcctaanag | gtgttccggn | cggcgttggg | gtcnctgcgg | a ggcggctaa | 120 |
| atcggccgca | gtttctncca | tggttgcgcc | cgctgtgttg | cgcgctctnc | g taagaacaa | 180 |
| gacccttcgc | tatggagttc | ccatgttgnt | gctggttgtn | agtggttctt | t tggtcttcg | 240 |
| cgaattt | | | | | | 248 |

<210> SEQ ID NO 41
<211> LENGTH: 352
<212> TYPE: DNA
<213> ORGANISM: Rattus norvegicus
<220> FEATURE:
<221> NAME/KEY: misc_feature
<223> OTHER INFORMATION: Incyte ID No: 70050103 3H1
<221> NAME/KEY: unsure
<222> LOCATION: 28, 324, 337
<223> OTHER INFORMATION: a, t, c, g, or o ther

<400> SEQUENCE: 41
ctctctgcct atgttctgag gttggagnct ttattacaga agctggtgca g aaaggagca   60
attgagaaag aagttgtgaa tcaggcccga ctagaccaag tcattgctgg g gcaatccac  120
aagtcagttc gaagagagct tggactgcca gaaggtagcc ctgccccagg c ttattgcag  180
ttgctgacac tgataaaaga taaggaggca gcagaggaag aggtccttct t caggccgaa  240
ttagaaggac atttcacttg acccaagacc agcaaggctg tcatgagcag a acatgatgg  300
aggagctcat agaagtgatc agcncatccc ctttggnctg ccaagtaatt g c          352

<210> SEQ ID NO 42
<211> LENGTH: 233
<212> TYPE: DNA
<213> ORGANISM: Rattus norvegicus
<220> FEATURE:
<221> NAME/KEY: misc_feature
<223> OTHER INFORMATION: Incyte ID No: 70013774 7H1

<400> SEQUENCE: 42
gtttctccat agcctcagac cccacatcag tatcctcttg ctacttggag g agcacgtga   60
gcaaagaggc taaccatcta atcagcaagt tccagaagct gatggcagag g ttggccact  120
tcgaaccagt caaccaggtg gtggaatcgg tggctaatgt catcggagcc a tgtgttttg  180
ggaagaactt cccaggaag agcgaggaga tgctcaacct cgtgaagagc a gc          233

<210> SEQ ID NO 43
<211> LENGTH: 243
<212> TYPE: DNA
<213> ORGANISM: Rattus norvegicus
<220> FEATURE:
<221> NAME/KEY: misc_feature
<223> OTHER INFORMATION: Incyte ID No: 70014170 8H1
<221> NAME/KEY: unsure
<222> LOCATION: 33
<223> OTHER INFORMATION: a, t, c, g, or o ther

<400> SEQUENCE: 43

```
tgggcagaaa ggaagccctg cagagcatca gangcccagc tagagggaca a cacagagga    60
gtaatttgct gacagacctg cagggatgga cctgctttca gctctcacac t ggaaacctg   120
ggtcctcctg gcagtcgtcc tggtgctcct ctacggattt gggacccgca c acatggact  180
tttcaagaaa caggggattc ctgggcccaa acctctgcct tttttttggca c tgtgctgaa  240
tta                                                                  243
```

<210> SEQ ID NO 44
<211> LENGTH: 295
<212> TYPE: DNA
<213> ORGANISM: Rattus norvegicus
<220> FEATURE:
<221> NAME/KEY: misc_feature
<223> OTHER INFORMATION: Incyte ID No: 70030245 4H1
<221> NAME/KEY: unsure
<222> LOCATION: 286
<223> OTHER INFORMATION: a, t, c, g, or o ther

<400> SEQUENCE: 44

```
gcgggccgtg ggtgatctgg tcggtaccgg agagcgcagg ttgtatcacc a acatggggg    60
actctcacga agacaccagt gccaccatgc ctgaggccgt ggctgaagaa g tgtctctat   120
tcagcacgac ggacatggtt ctgttttctc tcatcgtggg ggtcctgacc t actggttca   180
tctttagaaa gaagaaagaa gagataccgg agttcagcaa gatccaaaca a cggccccac   240
ccgtcaaaga gagcagcttc gtggaaaaga tgaagaaaac gggaangaac t tatc       295
```

<210> SEQ ID NO 45
<211> LENGTH: 286
<212> TYPE: DNA
<213> ORGANISM: Rattus norvegicus
<220> FEATURE:
<221> NAME/KEY: misc_feature
<223> OTHER INFORMATION: Incyte ID No: 70030440 5H1

<400> SEQUENCE: 45

```
cggaagtgaa ccaaggcact gagcggcatc taatgcacct ggagttggac a tctcagact    60
ccaagatcag gtatgaatct ggagatcacg tggctgtgta cccagccaat g actcagccc   120
tggtcaacca gattggggag atcctgggag ctgacctgga tgtcatcatg t tctaaaca   180
atctcgatga ggagtcaaac aagaagcatc cgttcccctg ccccaccacc t accgcacgg   240
ccctcaccta ctacctggac atcactaacc cgccacgcac caatgt                  286
```

<210> SEQ ID NO 46
<211> LENGTH: 311
<212> TYPE: DNA
<213> ORGANISM: Rattus norvegicus
<220> FEATURE:
<221> NAME/KEY: misc_feature
<223> OTHER INFORMATION: Incyte ID No: 70030609 6H1
<221> NAME/KEY: unsure
<222> LOCATION: 299
<223> OTHER INFORMATION: a, t, c, g, or o ther

<400> SEQUENCE: 46

```
gataggaaaa taattttatt taggttttttt aaaaaagtta actttcacat a taaatttag    60
acttaaagat tacagtgtat attttccaaa aggagcgccc ctgaagggtg g ccagacaag   120
ctcgccgagt gggcacaggg acactcgctc cagaaggagc tcaggtggaa g cgctttctt   180
taatcttcca cagtggccct tccctgttcc tcaccgggcc tatgactggt a agaaaaccc   240
```

```
-continued acaaccatca tttggggcaa cagcatctca ctagatggga ataagaacat g tctaggang      300 aaagcacaag c                                                            311

<210> SEQ ID NO 47
<211> LENGTH: 307
<212> TYPE: DNA
<213> ORGANISM: Rattus norvegicus
<220> FEATURE:
<221> NAME/KEY: misc_feature
<223> OTHER INFORMATION: Incyte ID No: 70032569 3H1

<400> SEQUENCE: 47
gtgccctcac gcagcttaat gtggccttt cccgggagca ggcccacaag g tctatgtcc        60 agcaccttct gaagagagac agggaacacc tgtggaagct gatccacgag g gcggtgccc      120 acatctatgt gtgcggggat gctcgaaata tggccaaaga tgtgcaaaac a cattctatg      180 acattgtggc tgagttcggg cccatggagc acacccaggc tgtggactat g ttaagaagc     240 tgatgaccaa gggccgctac tcactagatg tgtggagcta ggagcttacc a acctcccac     300 ccctcgg                                                                 307
```

TOXICOLOGICAL RESPONSE MARKERS

This application claims priority from provisional patent application U.S. Ser. No. 60/084,029 filed May 4, 1998, now abandoned.

FIELD OF THE INVENTION

The present invention relates to a composition for use in screening toxicological effects of test compounds or therapeutic treatments and methods employing such compositions.

BACKGROUND OF THE INVENTION

Toxicity testing is a necessary and time-consuming part of the pharmaceutical drug development pipeline. A more rapid screen to detect toxicity of lead drug candidates may be the use of gene expression microarrays. For example, microarrays consisting of full length genes or gene fragments on a substrate may be formed. These arrays can then be tested with samples treated with the drug candidates to elucidate the gene expression pattern associated with treatment with the drug candidate. This gene pattern can be compared with gene expression patterns of compounds associated with known toxicological responses.

Benzo(a)pyrene (BP) is a known rodent and likely human carcinogen and is the prototype of a class of compounds, the polycyclic aromatic hydrocarbons (PAHs). It is metabolized by several forms of cytochrome P450 and associated enzymes to both activated and detoxified metabolites (Degawa et al. (1994) Cancer Res. 54: 4915–4919). The ultimate metabolites are the bay-region diol epoxide, benzo(a)pyrene-7,8-diol-9,10-epoxide (BPDE) and the K-region diol epoxide, 9-hydroxy benzo(a)pyrene-4,5-oxide, which have been shown to form DNA adducts. BPDE-DNA adducts have been shown to persist in rat liver up to 56 days post dose with the treatment regimen of 10 mg/kg b.w. 3 times per week for 2 weeks (Qu and Stacey (1996) Carcinogenesis 17: 53–59). It has recently been shown that the BPDE-DNA adduct preferentially binds to methylated CpG sites in the p53 gene at sites where mutations are known to occur (Chen et al. (1998) Cancer Res. 58:2070–2075). Mutations in this tumor suppressor gene have been discovered in over 50% of human cancers (Greenblatt et al. (1994) Cancer Res. 54: 4855–4878).

Acetaminophen (APAP) is a well-recognized and widely-used analgesic. It is metabolized by specific cytochrome P450 isozymes with the majority of the drug undergoing detoxification by glucuronic acid, sulfate and glutathione conjugation pathways (Chen et al. (1998) Chem. Res. Toxicol. 11: 295–301). However, at large nontherapeutic doses, APAP can cause hepatic and renal failure by being metabolized to an active intermediate, N-acetyl-p-benzoquinone imine (NAPQI). NAPQI then binds to sulfhydryl groups of proteins causing their inactivation and leading to subsequent cell death (Kroger et al. (1997) Gen. Pharmacol. 28: 257–263).

Clofibrate (CLO) is an antilipidemic drug which lowers elevated levels of serum triglycerides. In rodents, chronic treatment produces hepatomegaly, an increase in hepatic peroxisomes and has been shown to be a hepatocarcinogen but not a mutagen (Lock et al. (1989) Ann. Rev. Pharmacol. Toxicol. 29:145). CLO has been shown to induce cytochrome P450 4A and reduce the levels of P450 4F (Kawashima et al. (1997) Arch. Biochem. Biophys. 347:148–154). It is also involved in transcription of b-oxidation genes as well as induction of peroxisome proliferator activated receptors (PPARs) (Kawashima supra).

The present invention provides compositions and methods for screening, preferably in a microarray format, of compounds and therapeutic treatments for toxicological effects.

SUMMARY OF THE INVENTION

In one aspect, the invention provides a method for screening a compound for a toxicological effect. The method comprises (i) selecting a plurality of polynucleotide targets, wherein said polynucleotide targets have first gene expression levels altered in tissues treated with known toxicological agents when compared with untreated tissues, (ii) treating a sample with the compound to induce second gene expression levels of a plurality of polynucleotide probes, and (iii) comparing the first and second gene expression levels to identify those compounds that induce expression levels of the polynucleotide probes that are similar to those of the polynucleotide targets and said similarity of expression levels correlates with a toxicological effect of the compound.

Preferably, the comparing comprises (i) contacting said polynucleotide targets with the polynucleotide probes under conditions effective to form hybridization complexes between said polynucleotide targets and said polynucleotide probes, and (ii) detecting the presence or absence of said hybridization complexes. In this context, similarity may mean that at least 1, preferably at least 5, more preferably 10, of the upregulated polynucleotide targets form hybridization complexes with the polynucleotide probes at least once during a time course to a greater extent than would the probes of a sample not treated with the test compound. Similarity may also mean that at least 1, preferably at least 3, of the downregulated polynucleotide target sequences form hybridization complexes with the polynucleotide probes at least once during a time course to a lesser extent than would the probes of a sample not treated with the test compound.

Preferred tissues are selected from the group consisting of liver, kidney, brain, spleen, pancreas and lung. Preferred toxicological agents are selected from the group consisting of benzo(a)pyrene, methylcholanthrene, benz(a)anthracene, 7,12-dimethylbenz(a)anthracene and their corresponding toxic metabolites. The polynucleotide targets comprise genes that are upregulated-or-down regulated at least 2 fold, preferably at least 3 fold, in tissues treated with known toxicological agents when compared with untreated tissues. Preferred polynucleotide targets are selected from the group consisting of SEQ ID NOs: 1–47, or fragments thereof, some of whose expression is upregulated and others of whose expression is downregulated. Even more preferable are SEQ ID NOs: 2, 8, 10, 13, 19, 26, 31, 33, 35, 37, 39, and 42 which are upregulated and SEQ ID Nos: 11, 25, 27, 28, and 45 which are downregulated. In one embodiment, the polynucleotide targets are hybridizable array elements of a microarray.

Alternatively, the invention provides methods for screening a therapeutic treatment for a toxicological effect or for screening a sample for a toxicological response to a compound or therapeutic treatment.

In another aspect, the invention provides methods for preventing a toxicological response by administering complementary nucleotide sequences against one or more selected upregulated polynucleotide target or a ribozyme that specifically cleaves such sequences. Alternatively, a toxicological response may be prevented by administering sense nucleotide sequences for one or more selected down regulated polynculeotide targets.

DESCRIPTION OF THE SEQUENCE LISTING

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The Sequence Listing contains the sequences of exemplary polynucleotide targets of the invention, SEQ ID NOs: 1–47.

DESCRIPTION OF THE INVENTION

Definitions

The term "microarray" refers to an ordered arrangement of hybridizable array elements. The array elements are arranged so that there are preferably at least one or more different array elements, more preferably at least 10 array elements, and most preferably at least 100 array elements, and even more preferably 10,000, on a 1 $cm^2$ substrate surface. Furthermore, the hybridization signal from each of the array elements is individually distinguishable. In a preferred embodiment, the array elements comprise polynucleotide sequences.

A "polynucleotide" refers to a chain of nucleotides. Preferably, the chain has from about 5 to 10,000 nucleotides, more preferably from about 50 to 3,500 nucleotides. The term "polynucleotide target" refers to a polynucleotide sequence capable of hybridizing with a "polynucleotide probe" to form a polynucleotide target/probe complex under hybridization conditions.

In some instances, the sequences will be complementary (no mismatches) when aligned. In other instances, there may be a substantial mismatch, up to 10%.

A "plurality" refers preferably to a group of one or more members, preferably to a group of at least about 10, and more preferably to a group of at least about 100 members, even more preferably a group of 10,000 members.

The term "gene" or "genes" refers to the partial or complete coding sequence of a gene. The term also refers to 5' or 3' untranslated regions. The gene may be in a sense or antisense configuration.

"Toxicological agent or compound" is any compound that elicits an unfavorable response in an individual or animal, such as DNA damage, organ damage, cell damage or cell death.

A "fragment" refers to a sequence which is a portion of a polynucleotide target sequence. Exemplary fragments are sequences comprising nucleotides 1–20 of SEQ ID Nos: 1–47.

The Invention

The present invention provides a composition and method for screening test compounds or therapeutic treatments for toxicological effects or for characterizing the toxicological responses of a sample to a test compound or a therapeutic treatment. In particular, the present invention provides a composition comprising a plurality of polynucleotide sequences derived from normal rat liver cDNA libraries, normalized rat liver cDNA libraries and prehybridized rat liver cDNA libraries and rat kidney libraries. The polynucleotide sequences have been further selected for exhibiting up-or-down regulated gene expression in rat liver samples when the rat liver samples have been exposed to a known toxin, in particular a hepatotoxin and more particularly a polycyclic aromatic hydrocarbon (PAH). PAHs include compounds such as benzo(a)pyrene, 3-methylcholanthrene, benz(a)anthracene, 7,12-dimethylbenz(a)anthracene, their corresponding metabolites, and the like. In a preferred embodiment the toxin is benzo(a)pyrene, or one of its toxic metabolites. The extent of upregulation or downregulation is at least 2 fold, more preferably at least 3 fold.

Exemplary polynucleotide sequences (targets) include SEQ ID NOs: 1–47 provided in the Sequence Listing or fragments thereof. These and other polynucleotide sequences can be immobilized on a substrate and used as hybridizable array elements in a microarray format. The microarray may be used to characterize gene expression patterns associated with novel compounds to elucidate any toxicological effects or to monitor the effects of therapeutic treatments where toxicological effects may be expected.

When the polynucleotide targets are employed as hybridizable array elements in a microarray, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a toxicological effect associated with a compound or a therapeutic treatment.

Furthermore, the present invention provides methods for screening compounds and/or therapeutic treatments for potential toxicological effects and for screening a sample's toxicological response to a particular test compound. Briefly, these methods entail treating a sample with the compound to be tested to elicit a change in gene expression patterns comprising the expression of a plurality of polynucleotide probes. Polynucleotide targets are selected by identifying those genes in rat liver or kidney that are up-or-downregulated at least 2 fold, more preferably at least 3 fold, when treated with a known toxic compound. Then, the polynucleotide targets and probes are combined under conditions effective to form hybridization complexes which may be detected by methods well known in the art. Detection of higher or lower levels of such hybridization complexes compared with hybridization complexes derived from samples treated with a compound that is known not to induce a toxicological effect correlates with a toxicological effect of a test compound or a toxicological response to a therapeutic treatment.

Sequences are identified that reflect all or most of the genes that are expressed in rat liver or kidney. Sequences may be identified by isolating clones derived from several types of rat cDNA libraries, including normal rat cDNA libraries, normalized rat cDNA libraries and prehybridized rat cDNA libraries. Clone inserts derived from these clones may be partially sequenced to generate expressed sequence tags (ESTs).

In one embodiment, two collections of ESTs are identified and sequenced. A first collection of ESTs (the originator sequences) are derived from rat liver and kidney and are derived from the cDNA libraries presented in the Examples. A second collection includes ESTs derived from other rat cDNA libraries available in the ZOOSEQ database (Incyte Genomics, Palo Alto, Calif.).

The two collections of ESTs are screened electronically to form master clusters of ESTs and then further analyzed as described below. Master clusters are formed by identifying overlapping EST sequences and assembling these ESTs. A nucleic acid fragment assembly tool, such as the Phrap tool (WashU-Merck) and the GELVIEW Fragment Assembly system (GCG), can be used for this purpose. The minimum number of clones necessary to constitute a cluster is two.

In another embodiment, a collection of human genes implicated in toxicology are used as the originator sequences and the collection of ESTs derived from the 55 rat cDNA libraries are again used as the additional sequences. Master clusters are formed around specific originator sequences, including the ESTs identified in rat liver and kidney or GenBank sequences which code for polypeptides implicated in toxicology in humans. After the sequences have been clustered, the most 5' clone is selected. After assembling the sequences, a representative clone is nominated from each master cluster. The most 5' clone is usually preferred because it is the one most likely to contain the complete gene. The nomination process is described in greater detail in "Relational Database and System for Storing Information Relating to Biomolecular Sequences and Reagents, Ser. No. 09/034,807, filed Mar. 4, 1998, herein incorporated in its entirety by reference.

Then, samples are treated, preferably at subchronic doses, with one or more known toxicological agents over a defined time course. Preferred toxicological agents are hepatotoxins, nephrotoxins, cardiotoxins and the like. Preferably, the agents are hepatotoxins, in particular members of the polycyclic aromatic hydrocarbon class. To this class belong benzo(a)pyrene, methylcholanthrene, benz(a)anthracene, 7,12-dimethylbenz(a)anthracene, their corresponding toxic metabolites, and the like. Alternatively, agents such as clofibrate and acetaminophen may be investigated.

The gene expression patterns derived from such treated biological samples can be compared with the gene expression patterns derived from untreated biological samples to identify genes whose expression is either upregulated or downregulated due to the presence of the toxins. These sequences may then be employed as array elements in a microarray alone or in combination with other array element sequences. Such a microarray is particularly useful to detect and characterize gene expression patterns associated with known toxicological agents. Such gene expression patterns can then be used for comparison to identify other compounds or therapeutic treatments which also elicit a toxicological response.

The selected polynucleotide sequences can be manipulated further to optimize the performance of the polynucleotide sequences as hybridization sequences. Some sequences may not hybridize effectively under hybridization conditions due to secondary structure. To optimize probe hybridization, the probe sequences are examined using a computer algorithm to identify portions of genes without potential secondary structure. Such computer algorithms are well known in the art, such as OLIGO 4.06 Primer Analysis Software (National Biosciences) or LASERGENE software (DNASTAR). These programs can search nucleotide sequences to identify stem loop structures and tandem repeats and to analyze G+C content of the sequence (those sequences with a G+C content greater than 60% are excluded). Alternatively, the sequences can be optimized by trial and error. Experiments can be performed to determine whether sequences and complementary target polynucleotides hybridize optimally under experimental conditions.

The polynucleotide sequences can be DNA or RNA, or any RNA-like or DNA-like material, such as mRNAs, cDNAs, genomic DNA, peptide nucleic acids, branched DNAs and the like. The polynucleotide sequences can be in sense or antisense orientations.

In one embodiment, the polynucleotide sequences are cDNAs. The size of the DNA sequence of interest may vary, and is preferably from 50 to 10,000 nucleotides, more preferably from 150 to 3,500 nucleotides. In a second embodiment, the polynucleotide sequences are vector DNAs. In this case the size of the DNA sequence of interest, i.e., the insert sequence, may vary from about 50 to 10,000 nucleotides, more preferably from about 150 to 3,500 nucleotides.

The polynucleotide sequences can be prepared by a variety of synthetic or enzymatic schemes which are well known in the art. (Caruthers et al. (1980) *Nucl. Acids Res. Symp. Ser.* 215–233). Nucleotide analogues can be incorporated into the polynucleotide sequences by methods well known in the art. The only requirement is that the incorporated nucleotide analogues must serve to base pair with polynucleotide probe sequences. For example, certain guanine nucleotides can be substituted with hypoxanthine which base pairs with cytosine residues. However, these base pairs are less stable than those between guanine and cytosine. Alternatively, adenine nucleotides can be substituted with 2,6-diaminopurine which can form stronger base pairs than those between adenine and thymidine. Additionally, the polynucleotide sequences can include nucleotides that have been derivatized chemically or enzymatically. Typical modifications include derivatization with acyl, alkyl, aryl or amino groups.

The polynucleotide sequences can be immobilized on a substrate via chemical bonding procedures. Furthermore, the sequences do not have to be directly bound to the substrate, but rather can be bound to the substrate through a linker group. The linker groups are typically about 6 to 50 atoms long to provide exposure to the attached polynucleotide probe. Preferred linker groups include ethylene glycol oligomers, diamines, diacids and the like. Reactive groups on the substrate surface react with one of the terminal portions of the linker to bind the linker to the substrate. The other terminal portion of the linker is then functionalized for binding the polynucleotide probe. Preferred substrates are any suitable rigid or semirigid support, including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the polynucleotide sequences are bound. Preferably, the substrates are optically transparent.

The samples can be any sample comprising polynucleotide probes and obtained from any bodily fluid (blood, urine, saliva, phlegm, gastric juices, etc.), cultured cells, biopsies, or other tissue preparations. The samples can be derived from humans or animal models.

DNA or RNA can be isolated from the sample according to any of a number of methods well known to those of skill in the art. For example, methods of purification of nucleic acids are described in *Laboratory Technicues in Biochemistry and Molecular Biology: Hybridization With Nucleic Acid Probes. Part I. Theory and Nucleic Acid Preparation*, P. Tijssen, ed. Elsevier (1993). In one preferred embodiment, total RNA is isolated using the TRIZOL total RNA isolation reagent (Life Technologies, Inc.) and mRNA is isolated using oligo d(T) column chromatography or glass beads. When polynucleotide probes are amplified it is desirable to amplify the nucleic acid sample and maintain the relative abundances of the original sample, including low abundance transcripts. RNA can be amplified in vitro, in situ or in vivo (See Eberwine U.S. Pat. No. 5,514,545).

It is also advantageous to include quantitation controls within the sample to assure that amplification and labeling procedures do not change the true distribution of polynucleotide probes in a sample. For this purpose, a sample is spiked with a known amount of a control polynucleotide and the composition of polynucleotide sequences includes reference polynucleotide sequences which specifically hybridize with the control target polynucleotides. After hybridization and processing, the hybridization signals obtained should reflect accurately the amounts of control polynucleotide added to the sample.

Prior to hybridization, it may be desirable to fragment the polynucleotide probes. Fragmentation improves hybridization by minimizing secondary structure and cross-hybridization to other polynucleotide probes in the sample or noncomplementary polynucleotide sequences. Fragmentation can be performed by mechanical or chemical means.

The polynucleotide probes may be labeled with one or more labeling moieties to allow for detection of hybridized probe/target polynucleotide complexes. The labeling moieties can include compositions that can be detected by spectroscopic, photochemical, biochemical, bioelectronic, immunochemical, electrical, optical or chemical means. The labeling moieties include radioisotopes, such as $^{32}$P, $^{33}$P or $^{35}$S, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like. Preferred fluorescent markers include C3 and C5 (Amersham).

Hybridization causes a polynucleotide probe and a complementary target polynucleotide to form a stable duplex through base pairing. Hybridization methods are well known to those skilled in the art (See, for example, *Laboratory Techniques in Biochemistry and Molecular Biology*, Vol. 24: *Hybridization With Nucleic Acid Probes*, P. Tijssen, ed. Elsevier, N.Y. (1993)). Conditions can be selected for hybridization where only fully complementary target and polynucleotide probe hybridize, i.e., each base pair must interact with its complementary base pair. Alternatively, conditions can be selected where target and polynucleotide sequences have mismatches but are still able to hybridize. Suitable conditions can be defined by salt concentration, temperature, and other chemicals and conditions well known in the art. Varying additional parameters, such as hybridization time, the concentration of detergent (sodium dodecyl sulfate, SDS) or solvent (formamide), and the inclusion or exclusion of carrier DNA, are well known to those skilled in the art. Additional variations on these conditions will be readily apparent to those skilled in the art (Wahl, G. M. and S. L. Berger (1987) Methods Enzymol. 152:399–407; Kimmel, A. R. (1987) Methods Enzymol. 152:507–511; Ausubel, F. M. et al. (1997) *Short Protocols in Molecular Biology*, John Wiley & Sons, New York, N.Y.; and Sambrook, J. et al. (1989) *Molecular Cloning. A Laboratory Manual*, Cold Spring Harbor Press, Plainview, N.Y.).

More particularly, hybridization can be performed with buffers, such as 5×SCC/0.1% SDS at 60° C. for about 6 hours. Subsequent washes are performed at higher stringency with buffers, such as 1×SCC/0.1% SDS at 45° C., then 0.1×SCC at to retain hybridization of only those target/probe complexes that contain exactly complementary sequences. Alternatively, salt concentration may be less than about 750 mM NaCl and 75 mM trisodium citrate, preferably less than about 500 mM NaCl and 50 mM trisodium citrate, and most preferably less than about 250 mM NaCl and 25 mM trisodium citrate. Stringent temperature conditions will ordinarily include temperatures of at least about 22° C., more preferably of at least about 37° C., and most preferably of at least about 42° C.

Hybridization specificity can be evaluated by comparing the hybridization of specificity-control polynucleotide sequences to specificity-control polynucleotide probes that are added to a sample in a known amount. The specificity-control target polynucleotides may have one or more sequence mismatches compared with the corresponding polynucleotide sequences. In this manner, whether only complementary target polynucleotides are hybridizing to the polynucleotide sequences or whether mismatched hybrid duplexes are forming is determined.

Hybridization reactions can be performed in absolute or differential hybridization formats. In the absolute hybridization format, polynucleotide probes from one sample are hybridized to the sequences in a microarray format and signals detected after hybridization complex formation correlate to polynucleotide probe levels in a sample. In the differential hybridization format, the differential expression of a set of genes in two biological samples is analyzed. For differential hybridization, polynucleotide probes from both biological samples are prepared and labeled with different labeling moieties. A mixture of the two labeled polynucleotide probes is added to a microarray. The microarray is then examined under conditions in which the emissions from the two different labels are individually detectable.

Sequences in the microarray that are hybridized to substantially equal numbers of polynucleotide probes derived from both biological samples give a distinct combined fluorescence (Shalon et al. PCT publication WO95/35505). In a preferred embodiment, the labels are fluorescent labels with distinguishable emission spectra, such as C3 and C5 fluorophores.

After hybridization, the microarray is washed to remove nonhybridized nucleic acids and complex formation between the hybridizable array elements and the polynucleotide probes is detected. Methods for detecting complex formation are well known to those skilled in the art. In a preferred embodiment, the polynucleotide probes are labeled with a fluorescent label and measurement of levels and patterns of fluorescence indicative of complex formation is accomplished by fluorescence microscopy, preferably confocal fluorescence microscopy.

In a differential hybridization experiment, polynucleotide probes from two or more different biological samples are labeled with two or more different fluorescent labels with different emission wavelengths. Fluorescent signals are detected separately with different photomultipliers set to detect specific wavelengths. The relative abundances/expression levels of the polynucleotide probes in two or more samples is obtained.

Typically, microarray fluorescence intensities can be normalized to take into account variations in hybridization intensities when more than one microarray is used under similar test conditions. In a preferred embodiment, individual polynucleotide probe/target complex hybridization intensities are normalized using the intensities derived from internal normalization controls contained on each microarray.

The composition comprising a plurality of polynucleotide target sequences can be used as hybridizable elements in a microarray. Such a microarray can be employed to identify expression profiles associated with particular toxicological responses. Then, a particular subset of these polynucleotide targets can be identified whose expression is altered in response to a particular toxicological agent. These polynucleotides can be employed to identify other compounds with a similar toxicological response.

Alternatively, for some treatments with known side effects, the microarray, and expression patterns derived therefrom, is employed to "fine tune" the treatment regimen. A dosage is established that minimizes expression patterns associated with undesirable side effects. This approach may be more sensitive and rapid than waiting for the patient to show toxicological side effects before altering the course of treatment. Generally, the method for screening a compound or therapeutic treatment to identify those with a potential toxicological effect entails selecting a plurality of polynucleotide targets which consist of genes whose gene expression levels are altered in tissues treated with known toxicological agents when compared with untreated tissues and treating a sample with the compound to induce a pattern of gene expression comprising the expression of a plurality of polynucleotide probes. A test compound may be screened at several doses to determine doses which may be toxic and other doses that may not.

Then, the expression levels of the polynucleotide targets and the polynucleotide probes are compared to identify those compounds that induce expression levels of the polynucleotide probes that are similar to those of the polynucleotide targets. In one preferred embodiment, gene expression levels are compared by contacting the polynucleotide targets with the polynucleotide probes under conditions effective to form hybridization complexes between polynucleotide targets and polynucleotide probes; and detecting the presence or absence of the hybridization complexes.

Similarity may mean that at least 1, preferably at least 5, more preferably 10, of the upregulated polynucleotide targets form hybridization complexes with the polynucleotide probes at least once during a time course to a greater extent than would the probes of a sample not treated with the test compound. Similarity may also mean that at least 1, preferably at least 3, of the downregulated polynucleotide target sequences form hybridization complexes with the polynucleotide probes at least once during a time course to a lesser extent than would the probes of a sample not treated with the test compound.

Such a similarity of expression patterns means that a toxicological effect is associated with the compound or therapeutic treatment tested. Preferably, the toxicological agents belong to the class of polycyclic aromatic hydrocarbons, including benzo(a)pyrene, methylcholanthrene, benz(a)anthracene, 7,12-dimethylbenz (a)anthracene, their corresponding toxic metabolites and the like. Of particular interest is the study of the toxic effects of these test compounds on the liver, kidney, brain, spleen, pancreas and lung.

It is understood that this invention is not limited to the particular methodology, protocols, and reagents described, as these may vary. It is also understood that the terminology used herein is for the purpose of describing particular embodiments only, and is not intended to limit the scope of the present invention which will be limited only by the appended claims. The examples below are provided to illustrate the subject invention and are not included for the purpose of limiting the invention.

EXAMPLES

Preparation and sequencing of cDNAs libraries have varied over time, and the gradual changes involved use of kits, plasmids, and machinery available at the particular time the library was made and analyzed.

I cDNA Library Construction

The RALINOT01 library was constructed from liver tissue removed from a pool of fifty 10- to 11-week-old Sprague-Dawley female rats (Charles River Laboratories, Wilmington, Mass.). The animals were housed in standard laboratory caging and fed PMI-certified Rodent Diet #5002. The animals appeared to be in good health at the time of harvest. The animals were anesthetized by $CO_2$ induction, and then cardiocentesis was performed. Other cDNA libraries were prepared as follows:

The RAKINOT01 library was constructed using 2.0 micrograms of polyA RNA isolated from kidney tissue removed from a pool of fifty, 7- to 8-week-old male Sprague-Dawley rats.

The RAKINOT02 library was constructed using 2.0 micrograms of polyA RNA isolated from kidney tissue removed from a pool of fifty, 10- to 11-week-old female Sprague-Dawley rats.

Frozen tissue was homogenized and lysed in TRIZOL reagent (1 gm tissue/10 ml TRIZOL; Cat. #10296-028; Life Technologies, Inc), a monoplastic solution of phenol and guanidine isothiocyanate, using a Brinkmann Homogenizer Polytron PT-3000 (Brinkmann Instruments, Westbury, N.Y.). After a brief incubation on ice, chloroform was added (1:5 v/v) and the lysate was centrifuged. The upper chloroform layer was removed to a fresh tube and the RNA extracted with isopropanol, resuspended in DEPC-treated water, and DNase treated for 25 min at 37° C. The RNA was re-extracted once with acid phenolchloroform pH 4.7 and precipitated using 0.3M sodium acetate and 2.5 volumes ethanol. The mRNA was then isolated using an OLIGOTEX kit (QIAGEN, Inc., Chatsworth, Calif.) and used to construct the cDNA library.

The MRNA was handled according to the recommended protocols in the SUPERSCRIPT Plasmid System for cDNA Synthesis and Plasmid Cloning (Life Technologies, Gaithersberg, Md.). The cDNAs were fractionated on a SEPHAROSE CL4B column (Amersham Pharmacia Biotech), and those cDNAs exceeding 400 bp were ligated into pINCY1 (Incyte Genomics). The plasmid pINCY1 was subsequently transformed into DH5α competent cells (Life Technologies).

II cDNA Library Normalization

In some cases, cDNA libraries were normalized in a single round according to the procedure of Soares et al. ((1994), *Proc. Natl. Acad. Sci.* 91: 9228–9232) with the following modifications. The primer to template ratio in the primer extension reaction was increased from 2:1 to 10:1. The dNTP concentration in the reaction was reduced to 150 µM each dNTP, allowing the generation of longer (400–1000 nt) primer extension products. The reannealing hybridization was extended from 13 to 19 hours. The single stranded DNA circles of the normalized library were purified by hydroxyapatite chromatography and converted to partially double-stranded by random priming, followed by electroporation into DH10B competent bacteria (Life Technologies).

The Soares normalization procedure is designed to reduce the initial variation in individual cDNA frequencies to achieve abundances within one order of magnitude while maintaining the overall sequence complexity of the library. In the normalization process, the prevalence of high-abundance cDNA clones decreases significantly, clones with mid-level abundance are relatively unaffected, and clones for rare transcripts are effectively increased in abundance. In the modified Soares normalization procedure, significantly longer hybridization times are used which allows for the increase of gene discovery rates by biasing the normalized libraries toward low-abundance cDNAs that are well represented in a standard transcript image.

The RALINON03 normalized rat liver library was constructed with $1.99 \times 10^6$ independent clones from the RALI- NOT01 library. Starting RNA was made from liver tissue removed from a pool of fifty, 10- to 11-week-old female Sprague Dawley rats. The library was normalized in one round using conditions adapted from Soares et al., *Proc. Natl. Acad. Sci.* (1994) 91: 9228–9232, except that a significantly longer (48-hour) reannealing hybridization was used.

The RALINON04 normalized rat liver library was constructed with $4.6 \times 10^5$ independent clones from RALINOT01. Starting RNA was made from liver tissue removed from a pool of fifty, 10- to 11-week-old female Sprague Dawley rats.

The RALINON07 normalized rat liver library was constructed with $1.99 \times 10^6$ independent clones from the RALINOT01 library. Starting RNA was made from liver tissue removed from a pool of fifty, 10- to 11-week-old female Sprague Dawley rats.

III CDNA Library Prehybridization

The RALINOH01 library was constructed with clones from RALINOT01. Starting RNA was made from liver tissue removed from a pool of fifty, 10- to 11-week-old female Sprague Dawley rats. After preparation of the cDNA library, 9,984 clones were spotted out onto a nylon filter, incubated, and processed to bind plasmid DNA to the filter. 10 mls of pre-warmed hybridization buffer per were added. The filter was hybridized in 0.75 M NaCl, 0.1 M Na2HPO4/NaH2PO4, 0.15 M Tris (pH 7.5), 5×Denhardt's Solution, 2% SDS, 100 µg/ml sheared salmon testes DNA, 50% formamide with $^{32}$P labeled sequences made from RALINOT01 at 42° C. for 14–16 hours. Then, filters were rinsed with 200 ml of 2×SSC at room temperature for 5 minutes. Filters were washed for 30 minutes at 68° C. with 200 ml of pre-warmed wash 1 (2×SSC, 1% SDS). A second wash was performed for an additional 30 minutes at 68° C. Filters were then washed with pre-warmed wash 2 (0.6×SSC, 1% SDS) for 30 minutes at 68° C. and repeat the process. 4,224 clones had very low hybridization signals and were selected for sequencing. About 20% of the clones do not have signals and these are isolated and sequenced.

IV Isolation and Sequencing of CDNA Clones

DNA was isolated using the following protocol. Single bacterial colonies were transferred into individual wells of the 384-well plates (Genetix Ltd, Christchurch, UK) using sterile toothpicks. The wells contained 1 ml of sterile Terrific Broth (BD Biosciences, Sparks Md.) with 25 mg/l carbenicillin and 0.4% glycerol (v/v). The plates were covered and placed in a THERMODYNE incubator (Newtown Square, Pa.) at 37° C. for 8–10 hours prior to use. Plasmid DNA was released from the cells and amplified using direct link PCR (Rao, V. B. (1994) *Anal. Biochem.* 216:1–14) as follows. The direct link PCR solution included 30 ml of Nucleix Plus PCR nucleotide mix (Catalog #4577235, Amersham Pharmacia Biotech) and 300 µl of Taq DNA polymerase (Catalog #0303Z, Amersham Pharmacia Biotech) with 12 µl Pfu DNA polymerase (Stratagene). Five µl of the PCR solution were added to each of the 384 wells using the HYDRA-96 microdispenser (Robbins Scientific, Sunnyvale Calif.); plates were centrifuged at 1000 rpm for 20 seconds and refrigerated until use. A 384 pin tool (V&P Scientific Inc, San Diego, Calif.) was used to transfer bacterial cells from the incubation plate into the plate containing the PCR solution where the component 0.1% Tween 20 caused the cells to undergo lysis and release the plasmid DNA. After lysis, the plates were centrifuged up to 500 rpm, covered with a cycle sealer, and cycled using a DNA ENGINE Thermal Cycler (MJ Research, Watertown, Mass.) using the program dPCR30 with the following parameters: Step 1) 95° C., 1 minute; Step 2) 94° C., 30 seconds; Step 3) 55° C., 30 seconds; Step 4) 72° C., 2 minutes; Step 5) steps 2, 3, and 4 repeated 29 times; Step 6) 72° C., 10 minutes; and Step 7) storage at 4° C.

The concentration of DNA in each well was determined by dispensing 100 µl Pico Green Dye Mix (0.25% (v/v) Pico Green Dye) (Molecular Probes, Eugene, Oreg.) dissolved in 1X TE and 0.5 µl of undiluted PCR product into each well of an opaque fluorimeter plate (Corning Costar, Acton, Mass.), allowing the DNA to bind to Pico Green Dye. The plate was scanned in a Flouroscan II (Labsystems Oy, Helsinki, FI) to measure the fluorescence of the sample and to quantitate the concentration of DNA. Typical concentrations of each DNA sample were in the range of 100 to 500 ng/ml.

The cDNAs were sequenced by the method of Sanger, F. and A. R. Coulson (*J. Mol. Biol.* (1975) 94:441–448), using either a MICROLAB 2200 system (Hamilton, Reno Nev.) or a HYDRA microdispenser (Robbins Scientific) in combination with DNA ENGINE Thermal Cyclers (MJ Research) and ABI 377 DNA Sequencing Systems (Applied Biosystems, Foster City, Calif.). Most of the isolates were sequenced according to standard ABI protocols, using ABI kits (Cat. #79345, 79339, 79340, 79357, 79355). Typically, 500 to 700 base pairs were sequenced in 3.5 to 4 hours. The solution volumes were used at 0.25×–1.0× concentrations. In the alternative, cDNAs may have been sequenced using solutions and dyes from Amersham Pharmacia Biotech.

The sequences derived from the sequencing of the clone inserts were used to populate the Zooseq database (Incyte Genomics).

V Rat Liver and Kidney Gene Selection

As a first step, originator sequences from high throughput sequencing experiments were derived from clone inserts from RALINOT01, RAKINOT01, RAKINOT02, RALINOH01, RALINON03, RALINON04 and RALINON07 CDNA library clones were obtained. There were 18,140 rat liver sequences and 5,779 rat kidney sequences.

Additionally, 1,500 rat sequences derived from clone inserts of any of 55 rat cDNA libraries were selected based on their homology to genes coding for polypeptides implicated in toxicological responses including peroxisome-associated genes, lysosome-associated genes, apoptosis-associated genes, p450 cytochromes, sulfotransferases, cysteine proteases, and the like.

Then, all the remaining sequences derived from all of the rat cDNA library clones were clustered based on the originator sequences described above. The clustering process involved identifying overlapping sequences that have a match quality indicated by a product score of 50 using BLAST. 6581 master clusters were identified.

After forming the clone clusters, a consensus sequence was generated based on the assembly of the clone sequences using Phrap. The assembled sequences were then annotated by first screening the assembled sequences against GenBank using BLASTn and then by screening the assembled sequences against GenPept using FASTX. About two thirds of the assembled sequences were annotated, about one third of the assembled sequences were not annotated.

VI Microarray Preparation

Clones nominated in the process described in Example VI were used to generate array elements. Each array element was amplified from bacterial cells. PCR amplification used primers complementary to the vector sequences flanking the cDNA insert. Array elements were amplified in thirty cycles of PCR from an initial quantity of 1–2 ng to a final quantity greater than 5 µg. Amplified array elements were then purified using Sephacryl-400 (Amersham Pharmacia Biotech, Piscataway, N.J.).

Purified array elements were immobilized on polymer-coated glass slides. Glass microscope slides (Corning, Corning, NY) cleaned by ultrasound in 0.1% SDS and acetone, with extensive distilled water washes between and after treatments. Glass slides were etched in 4% hydrofluoric acid (VWR, West Chester, Pa.), washed extensively in distilled water, and coated with 0 .05% aminopropyl silane (Sigma Aldrich, St. Louis, Mo.) in 95% ethyl alcohol. Coated slides were cured in a 110° C. oven.

Array elements were applied to the coated glass substrate using a procedure described in U.S. patent application, Ser. No. 08/477809, filed on Jun. 7, 1995, and incorporated herein by reference. In brief, 1 microliter of the array element DNA, at an average concentration of 0.5 µg/ml in 3×SSC, was loaded into the open capillary printing element by a high-speed robotic apparatus. The apparatus then deposited about 5 nl of array element sample per slide. A total of 7404 array elements representing rat liver and kidney genes and a variety of control elements, including 14 synthetic control sequences, human genomic DNA, and yeast genomic DNA, were arrayed in four identical quadrants within a 1.8 $cm^2$ area of the glass substrate.

Microarrays were UV-crosslinked using a STRATALINKER UV-crosslinker (Stratagene, La Jolla, Calif.). Microarrays were washed at room temperature once in 0.2% SDS and three times in distilled water. Non-specific binding sites were blocked by incubation of microarrays in 0.2% casein in phosphate buffered saline (PBS) (Tropix Inc., Bedford, Mass.) for 30 minutes. at 60° C. followed by washes in 0.2% SDS and distilled water as before.

VII Probe Preparation

Male Sprague-Dawley rats (6–8 wk old) were dosed with either benzo(a)pyrene (BP; Acros, Geel, Belgium) at 10 mg/kg body weight (bw) 3 times per week for 2 weeks, or dimethylsulfoxide (DMSO; Acros) at <2 ml/kg bw. Animals were monitored daily for physical condition and body weight, and blood samples were assayed for serum alanine transferase (ALT) and aspartate aminotransferase (AST) levels using a diagnostic kit (Sigma Aldrich). Three animals per group were sacrificed approximately 12 hours (h), 24 h, 72 h, 168 h, 336 h and 672 h following the last dose administered. Observed gross pathology and liver weights were recorded at time of necropsy. Liver, kidney, brain, spleen and pancreas from each rat were harvested, flash frozen in liquid nitrogen, and stored at −80° C.

Frozen liver was homogenized and lysed in TRIZOL reagent (Cat. #10296–028; Life Technologies) following the modifications for liver RNA isolation. Poly(A+) RNA was isolated using an OLIGOTEX kit (Qiagen, Carlsbad, Calif.) and labeled with either Cy3 or Cy5-labeled primers (Operon Technologies, Alameda, Calif.) using the GEMBRIGHT labeling kit (Incyte Genomics). MRNA isolated from tissues of rats dosed with PB was labeled with Cy5 and mRNA isolated from tissues of rats dosed with DMSO was labeled with Cy3. Quantitative and differential expression pattern control cDNAs were added to each labeling reaction. Labeled cDNA was treated with 0.5 M sodium bicarbonate (pH9.2) for 20 min at 85° C. to degrade the RNA and purified using two successive CHROMA SPIN 30 gel filtration spin columns (Clontech, Palo Alto, Calif.). Cy3 labeled control sample and Cy5 labeled experimental sample were combined and precipitated in glycogen, sodium acetate, and ethanol.

VIII Hybridization

Hybridization reactions contained 9 microliters of probe mixture consisting of 0.2 micrograms each of both Cy3 and Cy5 labeled cDNA synthesis products in 5×SSC, 0.2% SDS hybridization buffer. The probe mixture was heated to 65° C. for 5 min and was aliquoted onto the microarray surface and covered with an 1.8 $cm^2$ coverslip. The arrays were transferred to a waterproof chamber having a cavity just slightly larger than a microscope slide. The chamber was kept at 100% humidity internally by the addition of 140 microliters of 5×SSC in a corner of the chamber. The chamber containing the arrays was incubated for about 6.5 hours at 60° C. The arrays were washed for 10 min at 45° C. in low stringency wash buffer (1×SSC, 0.1% SDS), three times for 10 min each at 45 ° C. in high stringency wash buffer (0.1×SSC), and then dried.

IX Detection

The microscope used to detect the reporter-labeled hybridization complexes was outfitted with an Innova 70 mixed gas 10 W laser (Coherent Lasers, Santa Clara, Calif.) capable of generating spectral lines at 488 nm for excitation of Cy3, and 632 nm for excitation of Cy5. The excitation laser light was focused on the array using a 20X microscope objective (Nikon). The slide containing the array was placed on a computer-controlled X–Y stage on the microscope and raster-scanned past the objective. The 1.8 cm×1.8 cm array used in the present example was scanned with a resolution of 20 micrometers.

In two separate scans, a mixed gas multiline laser excited the two fluorophores sequentially. Emitted light was split, based on wavelength, into two photomultiplier tube detectors (PMT R1477, Hamamatsu Photonics, San Jose, Calif.) corresponding to the two fluorophores. Appropriate filters positioned between the array and the photomultiplier tubes were used to filter the signals. The emission maxima of the fluorophores used were 565 nm for Cy3 and 650 nm for Cy5. Each array was typically scanned twice, one scan per fluorophore using the appropriate filters at the laser source, although the apparatus was capable of recording the spectra from both fluorophores simultaneously.

The sensitivity of the scans was typically calibrated using the signal intensity generated by a cDNA control species added to the probe mix at a known concentration. A specific location on the array contained a complementary DNA sequence, allowing the intensity of the signal at that location to be correlated with a weight ratio of hybridizing species of 1:100,000. When two probes from different sources (e.g., representing test and control cells), each labeled with a different fluorophore, are hybridized to a single array for the purpose of identifying genes that are differentially expressed, the calibration was done by labeling samples of the calibrating cDNA with the two fluorophores and adding identical amounts of each to the hybridization mixture.

The output of the photomultiplier tube was digitized using a 12-bit RTI-835H analog-to-digital (A/D) conversion board (Analog Devices, Norwood, Mass.) installed in an IBM-compatible PC computer. The digitized data were displayed as an image where the signal intensity was mapped using a linear 20-color transformation to a pseudocolor scale ranging from blue (low signal) to red (high signal). The data was also analyzed quantitatively. Where two different fluorophores were excited and measured simultaneously, the data were first corrected for optical crosstalk (due to overlapping emission spectra) between the fluorophores using each fluorophore's emission spectrum.

A grid was superimposed over the fluorescence signal image such that the signal from each spot was centered in each element of the grid. The fluorescence signal within each element was then integrated to obtain a numerical value corresponding to the average intensity of the signal. The software used for signal analysis was the GEMTOOLS gene expression analysis program (Incyte Genomics).

X Results

The expression patterns of three cytochrome P450 isozymes known to be induced in a toxicological response were monitored during the 672 hour time course. The results are shown in Table 1.

TABLE 1

Gene expression patterns of known genes

| Gene | 12 hours | 1 day | 3 days | 7 days | 14 days | 28 days |
|---|---|---|---|---|---|---|
| P450 LA-omega | 1.2 | 2.3 | 2.4 | 1.4 | 6.8 | 1.2 |
| P450 MCA-inducible | 8.2 | 11.8 | 4.4 | 2.2 | 2.4 | 1.2 |
| P450 ISF/B-NF | 9.6 | 7.4 | 6.2 | 2.4 | 2.4 | 1.2 |

Each of the three genes was upregulated greater than 3 fold at least once during the time course.

We have discovered novel gene sequences that are up-regulated or downregulated at least 3 fold at least once during the time course. These sequences are SEQ ID NOs: 1–47 provided in the Sequence Listing. These polynucleotide sequences can be used for screening compounds or therapeutic treatments for a toxicologic effect. Table 2 shows the gene expression pattern of selected sequences that were upregulated at least 3 fold at least once during the time course.

TABLE 2

Gene expression patterns of upregulated polynucleotide targets

| SEQ ID NO: | 12 hours | 1 day | 3 days | 7 days | 14 days | 28 days |
|---|---|---|---|---|---|---|
| 2 | 3.4 | 1.9 | 0.7 | 0.5 | 1.99 | 0.77 |
| 8 | 1.6 | 3.2 | 1.2 | 1.1 | 3 | 1.5 |
| 10 | 2.8 | 5.9 | 3.2 | 2.1 | 2.9 | 1.8 |
| 13 | 2.9 | 6.1 | 3.1 | 2.3 | 3.3 | 1.9 |
| 19 | 2.7 | 3.5 | 3 | 1.9 | 1.7 | 1.5 |
| 26 | 1.1 | 4.7 | 1.5 | 1.3 | 5 | 2 |
| 31 | 2.3 | 3.8 | 1.6 | 2 | 1.7 | 2.1 |
| 33 | 2.1 | 4.1 | 3.2 | 2 | 1.7 | 1.6 |
| 35 | 1.2 | 3 | 5.1 | 1.4 | 5 | 1.3 |
| 37 | 3.4 | 0.5 | 0.6 | 0.7 | 0.9 | 0.5 |
| 39 | 1.5 | 3.5 | 1.8 | 1.5 | 3.5 | 2.1 |
| 42 | 9.1 | 9.1 | 5.2 | 2.4 | 2.1 | 1 |

Table 3 shows the gene expression pattern of selected sequences that were downregulated at least 3 fold at least once during the time course.

TABLE 3

Gene expression patterns of downregulated polynucleotide targets

| SEQ ID NO: | 12 hours | 1 day | 3 days | 7 days | 14 days | 28 days |
|---|---|---|---|---|---|---|
| 11 | 0.3 | 0.5 | 0.4 | 0.3 | 0.53 | 0.53 |
| 25 | 0.3 | 0.9 | 0.5 | 0.7 | 0.42 | 2.1 |
| 27 | 1 | 0.1 | 1 | 1.1 | 0.09 | 0.53 |
| 28 | 0.3 | 0.3 | 1.2 | 1.2 | 0.77 | 1.1 |
| 45 | 1.2 | 0.2 | 0.4 | 0.6 | 0.77 | 0.37 |

What is claimed is:

1. A composition comprising a plurality of polynucleotide targets, wherein each of said polynucleotide targets comprises a polynucleotide sequence of SEQ ID NO:8 and at least one polynucleotide sequence selected from the group consisting of SEQ ID NOs:1–7 and 9–47.

2. A composition comprising a plurality of polynucleotide targets, wherein said polynucleotide targets comprise SEQ ID NOs:1–47.

* * * * *